(12) United States Patent
Vogt et al.

(10) Patent No.: US 8,598,251 B2
(45) Date of Patent: Dec. 3, 2013

(54) PASTE-LIKE BONE CEMENT

(75) Inventors: Sebastian Vogt, Erfurt (DE); Hubert Büchner, Nürnberg (DE)

(73) Assignee: Heraeus Medical GmbH, Wehrheim (DE)

(*) Notice: Subject to any disclaimer, the term of this patent is extended or adjusted under 35 U.S.C. 154(b) by 0 days.

(21) Appl. No.: 13/162,735

(22) Filed: Jun. 17, 2011

(65) Prior Publication Data

US 2011/0313078 A1   Dec. 22, 2011

(30) Foreign Application Priority Data

Jun. 22, 2010   (DE) .......................... 10 2010 024 653

(51) Int. Cl.
*A61L 24/06* (2006.01)

(52) U.S. Cl.
USPC ......................................... 523/116; 523/115

(58) Field of Classification Search
USPC .................................................. 523/115, 116
See application file for complete search history.

(56) References Cited

U.S. PATENT DOCUMENTS

| | | | | |
|---|---|---|---|---|
| 3,347,954 A * | 10/1967 | Bredereck et al. | ............... | 525/21 |
| 4,015,945 A | 4/1977 | Frankel et al. | | |
| 4,767,798 A * | 8/1988 | Gasser et al. | ................. | 523/117 |
| 5,252,629 A * | 10/1993 | Imai et al. | ...................... | 523/118 |
| 5,688,883 A | 11/1997 | Klee et al. | | |
| 6,096,842 A | 8/2000 | Friese et al. | | |
| 6,833,425 B1 * | 12/2004 | Hecht et al. | ...................... | 528/71 |
| 6,852,775 B1 * | 2/2005 | Soglowek et al. | ............ | 523/109 |
| 6,871,996 B2 | 3/2005 | Jonsson | | |
| 6,953,535 B2 * | 10/2005 | Hecht et al. | ............... | 252/183.13 |
| 6,998,111 B2 * | 2/2006 | Klee et al. | ......................... | 424/49 |
| 7,456,232 B2 * | 11/2008 | Mikulla et al. | ................. | 523/115 |
| 7,989,519 B2 * | 8/2011 | Vogt et al. | ...................... | 523/115 |
| 8,129,444 B2 * | 3/2012 | Hecht et al. | ...................... | 523/115 |
| 8,426,490 B2 * | 4/2013 | Bissinger et al. | ............. | 523/117 |
| 2003/0195273 A1 | 10/2003 | Mitra et al. | | |
| 2006/0004122 A1* | 1/2006 | Hecht et al. | ...................... | 523/115 |
| 2007/0040151 A1 | 2/2007 | Utterodt et al. | | |
| 2009/0105144 A1* | 4/2009 | Vogt et al. | ........................ | 514/12 |
| 2009/0105366 A1* | 4/2009 | Vogt et al. | ...................... | 523/116 |
| 2009/0105367 A1* | 4/2009 | Vogt et al. | ...................... | 523/116 |
| 2010/0159027 A1* | 6/2010 | Vogt et al. | ...................... | 424/615 |

FOREIGN PATENT DOCUMENTS

| | | |
|---|---|---|
| DE | 1495520 A1 | 4/1969 |
| DE | 19501933 A1 | 7/1996 |
| DE | 69621500 T2 | 1/2003 |
| DE | 10 2007 052 116 A1 | 4/2009 |
| DE | 102007050763 A1 | 4/2009 |
| DE | 10 2007 050 762 B3 | 5/2009 |
| EP | 0674888 A1 | 10/1995 |
| EP | 1479364 A1 | 11/2004 |
| EP | 1754465 A1 | 2/2007 |
| GB | 2256875 A | 12/1992 |
| JP | 2003181270 A | 7/2003 |
| JP | 2009-101159 A | 5/2009 |
| JP | 2009-101160 A | 5/2009 |
| JP | 2009-102640 A | 5/2009 |
| WO | 2007140440 A2 | 12/2007 |

OTHER PUBLICATIONS

Material Data Sheet for Aliquat 336 revision date Aug. 2, 2000, Acros Organics N. V.*
Office Action issued Jan. 28, 2011 in DE Application No. 10 2010 024 653.0.
Charnley, "Anchorage of the Femoral Head Prosthesis to the Shaft of the Femur," The Journal of Bone and Joint Surgery, vol. 42B, No. 1, pp. 28-30 (1960).
Office Action issued Dec. 4, 2012 in Canadian Application No. 2,742,537.
English translation of an Office Action issued Apr. 22, 2013 in corresponding Chinese patent application No. 201110169272.0.
English translation of an Office Action issued Jul. 2, 2013 in JP Application No. 2011-132322.

* cited by examiner

*Primary Examiner* — James J. Seidleck
*Assistant Examiner* — Peter A Salamon
(74) *Attorney, Agent, or Firm* — Panitch Schwarze Belisario & Nadel LLP

(57) ABSTRACT

A kit is provided based on two pastes designed to produce bone cement with high initial stability and therefore low post-cure. The kit includes a paste A and a paste B, wherein paste A contains (a1) a polymerizable monomer having a pH in water in the range of 5-9, (a2) a filling agent insoluble in (a1), and (a3) a barbituric acid derivative selected from the group consisting of 1,5-disubstituted barbiturates, 1,3,5-trisubstituted barbiturates, and 1,3,5-tetrasubstituted barbiturates, and paste B contains (b1) a polymerizable monomer having a pH in water in the range of 5-9, (b2) a filling agent insoluble in (b1), (b3) a peroxide soluble in (b1), (b4) a heavy metal compound insoluble in (b1) and selected from the group consisting of heavy metal salts and heavy metal complexes, and wherein at least one of the pastes A and B contains a halide salt.

14 Claims, No Drawings

PASTE-LIKE BONE CEMENT

BACKGROUND OF THE INVENTION

The present invention relates to a kit for producing bone cement and use of the kit.

Conventional polymethylmethacrylate bone cements (PMMA bone cements) have been known for decades and are based on the ground-breaking work of Sir Charnley (Charnley, J., "Anchorage of the femoral head prosthesis of the shaft of the femur," *J. Bone Joint Surg.*, 42:28-30 (1960)). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers made by polymerization, preferably suspension polymerization, based on methylmethacrylate and co-monomers, such as styrene, methylacrylate or similar monomers, (ii) a radio-opacifier, and (iii) an initiator, (for example) dibenzoylperoxide. Mixing the powder component and the monomer component, the polymers of the powder component swell in the methylmethacrylate swell, which generates a dough that can be shaped plastically. Simultaneously, the activator, N,N-dimethyl-p-toluidine, reacts with dibenzoylperoxide, which disintegrates and forms radicals in the process. The radicals thus formed trigger the radical polymerization of the methylmethacrylate. Upon advancing polymerization of the methylmethacrylate, the viscosity of the cement dough increases until the cement dough solidifies and thus is cured.

The essential disadvantage of the previous PMMA bone cements for the medical user is that the user needs to mix the liquid monomer component and the powder component in a mixing system or in crucibles right before applying the cement. Mixing error can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in U.S. Pat. No. 4,015,945, European patent application publication EP 0 674 888 A1, and Japanese patent application publication (kokai) JP 2003/181270.

However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel are required for this purpose. The corresponding training is associated with considerable expense. Moreover, mixing of the liquid monomer component and the powder component is associated with exposure of the user to monomer vapors and particles released from the powder-like cement.

Paste-like polymethylmethacrylate bone cements, as an alternative to the conventional powder-liquid polymethylmethacrylate bone cements, have been described in unexamined German patent applications DE 10 2007 052 116 A1 and DE 10 2007 050 763 A1. The bone cements are provided to the user in the form of pre-mixed pastes that are stable during storage. In the case of paste-like two-component cements, the initiator and the accelerator are each dissolved separately in one cement paste. When the two pastes are mixed, the accelerator reacts with the initiator forming radicals that initiate the radical polymerization of the monomer in the paste. This starts the curing of the cement paste. In the case of paste-like one-component systems, the polymerization can be triggered by thermally disintegrating initiators through the action of magnetic or electromagnetic fields on ferromagnetic particles or superparamagnetic particles contained in the paste.

Initiator systems for radical polymerization of methacrylate monomers and other monomers susceptible to radical polymerization have been known for a long time.

Accordingly, German Patent DE 696 21 500 T2 discloses a combination of peroxides and metal compounds. A combination of cumene hydroperoxide, a metal compound, and thiourea is used in this context. A similar combination of thiourea and a hydroperoxide is proposed in European patent application publication EP 1 479 364 A1. In contrast, German published patent application DE 195 01 933 A1 discloses mixtures of hydroperoxides and siccatives. An interesting new system based on hydroperoxides, acylthiourea compounds, and copper salts is presented in European patent application publication EP 1 754 465 A1. The advantage of initiator systems of this type is their high thermal stability. However, hydroperoxides are irritating compounds and thus suitable only to a limited extent for initiation with PMMA bone cements directly contacting vital bone tissue.

Used with conventional PMMA bone cements that consisted of a powder component and a monomer liquid, the initiator system of dibenzoylperoxide and N,N-dimethyl-p-toluidine has proven its value in general (K.-D. Kühn, *Knochenzemente für die Endoprothetik: ein aktueller Vergleich der physikalischen and chemischen Eigenschaften handelsüblicher PMMA-Zemente* [Bone Cements For Endoprosthetics: An Actual Comparison of The Physical and Chemical Properties of Commercial PMMA Cements], Springer-Verlag, Berlin Heidelberg New York (2001)). In this context, dibenzoylperoxide is present as a solid in the cement powder and N,N-dimethyl-p-toluidine is dissolved in the monomer component.

However, our experiments with cement pastes using the dibenzoylperoxide/N,N-dimethyl-p-toluidine initiator system demonstrated that pastes containing N,N-dimethyl-p-toluidine have a pronounced tendency to polymerize spontaneously. Moreover, the accelerator, N,N-dimethyl-p-toluidine, that has proven its value with conventional powder/liquid polymethylmethacrylate bone cements has been the subject of some criticism due to its toxicological properties.

Aside from these redox systems, initiator systems based on the use of barbiturates have also been described. German published patent application DE 1 495 520 A1 describes a method for polymerization of vinyl compounds and polyesters. In the method, barbituric acid derivatives, halide ion donors, and copper compounds are dissolved in the monomer or mixture of monomers. In this context, the combination of barbituric acid derivative, halide ion donor, and copper compound initiates the polymerization. It is also feasible to add organic peroxides or hydrogen peroxide. Our own experiments in this context showed that initiation is also feasible in the absence of atmospheric oxygen or peroxides, which is contrary to the assumption made in DE 1 495 520, according to which air or peroxides are required to trigger the polymerization by barbiturate in the presence of copper ions and chloride ions. This means that the barbiturate itself obviously acts as initiator.

U.S. patent application publication 2003/0195273 A1 proposes a curable composition for dental applications that contains not only unsaturated monomers, but also water, a redox initiator system, and ammonium salts. The initiator system that is based on barbiturates and known from DE 1 495 520 is mentioned in this context as well.

A primer based on a monomer that can be mixed with water, a copper salt, a chloride ion donor, and thiobarbiturates as well as barbiturates has been disclosed in UK patent application publication GB 2 256 875 A. There is no evidence of the use of copper(II) hydroxide or basic copper carbonate.

A very interesting system is described in International Publication No. WO 2007/140440 A2, in which an alkali salt or alkaline earth salt of barbituric acid that is insoluble in non-acidic monomers is used in pastes. Acidic monomers acting on the barbituric acid salts release the barbiturates through a cation exchange. The barbiturates thus released react in the presence of halide ion donors with dissolved copper ions that are present in the pastes and thus initiate the radical polymerization.

A somewhat more complex system is described in DE 10 2007 050 763. In this system, alkaline earth salts of barbiturates and basic copper salts are contained in one paste. These two salts are insoluble in the methacrylate monomer. A weak organic acid, such as 2-ethylhexanoic acid, is present in a second paste. Moreover, a chloride ion donor is also present in the pastes. Mixing the two pastes, the weak organic acid simultaneously converts both the barbiturate into the soluble acid form and copper into a soluble copper salt. The advantage of this system, in particular in the case of pastes with multi-functional monomers, is that earlier diffusion and ion exchange processes allow the processing time to be increased, which otherwise is very short, usually on the order of seconds, where multi-functional monomers are used.

DE 10 2007 050 762 discloses another system for the producing bone cement. The invention described therein is based on the approach of providing two pastes which each contain a methacrylate monomer, in which a polymer that is soluble therein is dissolved and a polymer that is insoluble therein is suspended. This allows a dough-like paste to be produced that shows high internal cohesion due to the polymer being dissolved therein. In order to cure the methacrylate monomer, one of the pastes contains a radical initiator, for example a barbituric acid derivative, and the other paste contains an accelerator, for example an organic copper(II) salt. After the two pastes are mixed, activation of the initiator starts the polymerization of the methacrylate monomer, which involves the formation of bone cement with high 4-point flexural strength and high flexural modulus.

Experiments involving the use of paste-like, two-component cements containing filling agents insoluble in the methacrylate monomer, for example polymer particles, demonstrated low initial stability and an ensuing pronounced tendency to show post-cure. This effect is due to monomer that is contained in the insoluble filling agents. During the curing process, the monomer polymerizes mainly outside of the insoluble polymer particles. Subsequently, the residual monomer, as well as the dissolved initiator or the dissolved accelerator, diffuse from the polymer particles, and the monomer is then subject to post-cure. Experiments have shown that the post-cure effect is mainly caused by the paste in which the accelerator is dissolved. For this reason, it would be advantageous of providing both pastes of the two-component bone cement with initiators, if possible. However, this is associated with a technical contradiction in that the accelerator needs to make both initiators form radicals, but must, on the other hand, not trigger premature polymerization while the cement pastes are being stored.

BRIEF SUMMARY OF THE INVENTION

The present invention was therefore based on the object of providing a kit based on two pastes designed to produce bone cement with high initial stability and therefore low post-cure.

The object is achieved by a kit comprising a paste A and a paste B, wherein:
(a) paste A contains:
(a1) a polymerizable monomer having a pH in water in the range of 5-9;
(a2) a filling agent insoluble in (a1); and
(a3) a barbituric acid derivative selected from the group consisting of 1,5-disubstituted barbiturates, 1,3,5-trisubstituted barbiturates, and 1,3,5-tetrasubstituted barbiturates, and
(b) paste B contains:
(a1) a polymerizable monomer having a pH in water in the range of 5-9;
(b2) a filling agent insoluble in (b1);
(b3) a peroxide soluble in (b1);
(b4) a heavy metal compound insoluble in (b1) and selected from the group consisting of heavy metal salts and heavy metal complexes,
wherein at least one of the pastes A and B contains a halide salt.

The invention is based on the idea to use, in one paste, a peroxide-type initiator dissolved in the methacrylate monomer and, in addition, to suspend in the paste a basic heavy metal salt insoluble in the methacrylate monomer. It has been evident surprisingly that insoluble heavy metal salts, such as copper(II) hydroxide, that are suspended in the methacrylate monomer do not disintegrate the peroxide dissolved in the methacrylate monomer. Accordingly, there is no spontaneous polymerization in the paste.

The invention is further based on the idea of using a second paste that contains a barbiturate soluble in methylmethacrylate. Mixing the two pastes, the soluble barbiturate reacts with the basic heavy metal salt due to its acidity. It has been found surprisingly that this allows to initiate the polymerization reaction in the presence of a soluble halide ion donor. The action of the barbiturate on the basic heavy metal salt obviously transitions the heavy metal ions into a soluble salt form which initiates the polymerization of the methacrylate monomer through its action on barbituric acid and the peroxide. In this context, the use of aromatic amines as accelerators is no longer required.

Consequently, the paste-like components of the kit for producing bone cement each contain an initiator (barbituric acid derivative and/or peroxide) and, in at least one of these paste-like components, an accelerator (insoluble heavy metal compound). Surprisingly, there is no undesired premature polymerization before the targeted mixing of the two pastes. This overcomes the technical contradiction being that the accelerator, on the one hand, needs to make both initiators form radicals, but must, on the other hand, not trigger premature polymerization while the cement pastes are being stored. Use of the initiator system according to the invention and provision of a polymerization initiator in each of the kit components allows high initial stability of the bone cement to be attained and pronounced post-cure of the bone cement to be prevented.

According to the invention, a kit shall be understood to be a system made up of at least two components. Although reference to two components is made in the following, the kit can just as well contain more than two components, for example three, four, five or more than five components, according to need. The individual components preferably are packaged separate from each other, such that the ingredients of the one kit component do not contact the ingredients of another kit component. Accordingly, it is feasible, for example, to package the kit components separate from each other and store them together in a reservoir container.

DETAILED DESCRIPTION OF THE INVENTION

According to the invention, the kit comprises at least one paste A and one paste B.

Paste A contains at least one polymerizable monomer (a1) having a pH in water in the range of 5-9. Preferably, the polymerizable monomer (a1) is liquid at a temperature of 25° C. and a pressure of 1013 hPa.

The polymerizable monomer (a1) preferably is a methacrylic acid ester. Preferably, the methacrylic acid ester (a1) is a monofunctional methacrylic acid ester. The monofunctional methacrylic acid ester preferably is hydrophobic. The use of hydrophobic monofunctional methacrylic acid esters (a1) allows later enlargement of the volume of the bone cement due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1-20 carbon atoms, more preferably 1-10 carbon atoms, even more preferably 1-6 carbon atoms, and particularly preferably 1-4 carbon atoms. The alcohols can be substituted or non-substituted and preferably are non-substituted. Moreover, the alcohols can be saturated or unsaturated and preferably are saturated.

According to a particularly preferred embodiment, the polymerizable monomer (a1) is methacrylic acid methylester and methacrylic acid ethylester. According to a further particularly preferred embodiment, the polymerizable monomer (a1) is not a bisphenol A-derived methacrylic acid ester.

The polymerizable monomer (a1) used according to the invention preferably has a molar mass of less than 1,000 g/mol. This also comprises polymerizable monomers that are components of a mixture of monomers, wherein at least one of the polymerizable monomers of the mixture of monomers has a defined structure with a molar mass of less than 1,000 g/mol.

The polymerizable monomer (a1) is characterized in that an aqueous solution of the polymerizable monomer (a1) has a pH in the range of 5-9, preferably in the range of 5.5-8.5, even more preferably in the range of 6-8, and particularly preferably in the range of 6.5-7.5.

Paste A preferably contains 15-85% by weight, more preferably 20-70% by weight, even more preferably 25-60% by weight, and particularly preferably 25-50% by weight of at least one polymerizable monomer (a1), relative to the total weight of the components contained in paste A. Accordingly, paste A can contain one or more polymerizable monomers (a1) that differ in structure.

Moreover, paste A contains at least one filling agent (a2) that is insoluble in (a1).

The filling agent (a2) is a solid substance at room temperature that is capable of increasing the viscosity of the mixture made up of the other components contained in paste A. The filling agent (a2) should be biocompatible. According to a preferred embodiment, the filling agent (a2) is selected from polymers, inorganic salts, inorganic oxides, metals, and metal alloys.

The filling agent (a2) preferably is particulate. According to a particularly preferred embodiment, the filling agent (a2) has an average particle size in the range of 10 nm-100 µm and particularly preferably in the range of 100 nm-10 µm. The average particle size shall be understood herein to mean a size range that applies to at least 90 percent of the particles.

In the scope of the invention, the term "polymers" for filling agent (a2) shall include both homopolymers and copolymers.

The polymer used as filling agent preferably is a polymer having a mean (by weight) molar mass of at least 150,000 g/mol. The specification of the molar mass refers to the molar mass determined by viscosimetry. The polymer can, for example, be a polymer or copolymer of a methacrylic acid ester. According to a particularly preferred embodiment, the at least one polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), and poly(styrene-co-methylmethacrylate). However, the polymer can just as well be selected from the group consisting of polyethylene, polypropylene or polybutadiene. Moreover, the paste can be cross-linked or non-cross-linked.

The inorganic salt that can be used as filling agent (a2) can be a salt that is soluble or insoluble in the polymerizable monomer. Preferably, the inorganic salt is a salt of an element selected from the second main group of the Periodic Table of elements. According to a preferred embodiment, the inorganic salt is a calcium, strontium or barium salt. According to a particularly preferred embodiment, the inorganic salt is calcium sulfate, barium sulfate or calcium carbonate.

The inorganic oxide that can be used as filling agent (a2) can preferably be a metal oxide. According to a preferred embodiment, the inorganic oxide is a transition metal oxide. According to a particularly preferred embodiment, the inorganic oxide is titanium dioxide or zirconium dioxide.

The metal that can be used as filling agent (a2) can, for example, be a transition metal. According to a preferred embodiment, the metal is tantalum or tungsten.

The metal alloy that can be used as filling agent (a2) is an alloy of at least two metals. Preferably, the alloy contains at least one transition metal. According to a particularly preferred embodiment, the alloy comprises at least tantalum or tungsten. The alloy can also be an alloy of tantalum and tungsten.

The filling agent (a2) is insoluble in the polymerizable monomer (a1) having a pH in the range of 5-9. According to the invention, the filling agent (a2) is considered insoluble in the polymerizable monomer having a pH in the range of 5-9 (a1), if the solubility of the filling agent (a2) in the polymerizable monomer (a1) at a temperature of 25° C. is less than 50 g/l, preferably is less than 25 g/l, more preferably is less than 10 g/l, and even more preferably is less than 5 g/l.

The fraction of the at least one filling agent (a2) preferably is less than 85% by weight, more preferably is less than 80% by weight, and even more preferably is less than 75% by weight, relative to the total weight of the components contained in paste A. Paste A preferably contains 15-85% by weight, more preferably 15-80% by weight, and even more preferably 20-75% by weight of the at least one filling agent (a2), relative to the total weight of the components contained in paste A.

Moreover, paste A contains at least one barbituric acid derivative (a3). The barbituric acid derivative (a3) is selected from the group consisting of 1,5-disubstituted barbiturates, 1,3,5-trisubstituted barbiturates, and 1,3,5-tetrasubstituted barbiturates.

According to a preferred embodiment, the barbituric acid derivative (a3) is soluble in the polymerizable monomer (a1). The barbituric acid derivative (a3) is considered soluble in the polymerizable monomer (a1) if at least 1 g/l, preferably at least 3 g/l, even more preferably at least 5 g/l, and particularly preferably at least 10 g/l of the barbituric acid derivative (a3), dissolve(s) in the polymerizable monomer (a1) at a temperature of 25° C.

There is no limitation with regard to the type of substituents on the barbituric acid. The substituents can be, for example, aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred.

According to a preferred embodiment, the substituents each have a length of 1-10 carbon atoms, more preferably a length of 1-8 carbon atoms, and particularly preferably a length in the range of 2-7 carbon atoms.

Barbiturates having one substituent each at position 1 and position 5, one substituent each at positions 1, 3, and 5 or one substituent each at positions 1 and 3 and two substituents at position 5 are preferred according to the invention.

According to another preferred embodiment, the barbituric acid derivative is a 1,5-disubstituted barbiturate or a 1,3,5-trisubstituted barbiturate. 1,3,5-tetrasubstituted barbiturates can also be used, although they are capable of crossing the blood-brain barrier and thus possess pharmacological activity.

According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

The fraction of paste A accounted for by the at least one barbituric acid derivative (a3) preferably is in the range from 0.1-10% by weight, more preferably in the range from 0.5-8% by weight, and even more preferably in the range of 1-5% by weight, relative to the total weight of the components contained in paste A.

Paste A preferably is essentially free of heavy metal compounds. The term "heavy metal compounds" in this context shall mean metals having a density of at least 3.5, preferably of at least 5, at a temperature of 20° C. The fraction of paste A accounted for by heavy metal compounds preferably is less than 50 ppm, more preferably is less than 25 ppm, even more preferably is less than 10 ppm, and particularly preferably is less than 5 ppm.

Paste B contains at least one polymerizable monomer (b1) having a pH in water in the range of 5-9.

Preferably, the polymerizable monomer (b1) is liquid at a temperature of 25° C. and a pressure of 1013 hPa.

The polymerizable monomer (b1) preferably is a methacrylic acid ester. Preferably, the methacrylic acid ester (b1) is a monofunctional methacrylic acid ester. The monofunctional methacrylic acid ester preferably is hydrophobic. The use of hydrophobic monofunctional methacrylic acid esters (b1) allows later enlargement of the volume of the bone cement due to the uptake of water and thus damage to the bone to be prevented. According to a preferred embodiment, the monofunctional methacrylic acid ester is considered hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1-20 carbon atoms, more preferably 1-10 carbon atoms, even more preferably 1-6 carbon atoms, and particularly preferably 1-4 carbon atoms. The alcohols can be substituted or non-substituted and preferably are non-substituted. Moreover, the alcohols can be saturated or unsaturated and preferably are saturated.

According to a particularly preferred embodiment, the polymerizable monomer (a1) is methacrylic acid methylester and methacrylic acid ethylester. According to a further particularly preferred embodiment, the polymerizable monomer (a1) is not a bisphenol A-derived methacrylic acid ester.

The polymerizable monomer (b1) used according to the invention preferably has a molar mass of less than 1,000 g/mol. This also comprises polymerizable monomers that are components of a mixture of monomers, wherein at least one of the polymerizable monomers of the mixture of monomers has a defined structure with a molar mass of less than 1,000 g/mol.

The polymerizable monomer (b1) is characterized in that an aqueous solution of the polymerizable monomer (b1) has a pH in the range of 5-9, preferably in the range of 5.5-8.5, even more preferably in the range of 6-8, and particularly preferably in the range of 6.5-7.5.

Paste B preferably contains 15-85% by weight, more preferably 20-70% by weight, even more preferably 25-60% by weight, and particularly preferably 25-50% by weight of at least one polymerizable monomer (b1), relative to the total weight of the components contained in paste B. Accordingly, paste B can contain one or more polymerizable monomers (b1) that differ in structure.

Moreover, paste B contains at least one filling agent (b2) that is insoluble in (b1).

The filling agent (b2) is a solid substance at room temperature that is capable of increasing the viscosity of the mixture made up of the other components contained in paste B. The filling agent (b2) should be biocompatible. According to a preferred embodiment, the filling agent (b2) is selected from polymers, inorganic salts, inorganic oxides, metals, and metal alloys.

The filling agent (b2) preferably is particulate. According to a particularly preferred embodiment, the filling agent (b2) has an average particle size in the range of 10 nm-100 µm and particularly preferably in the range of 100 nm-10 µm. The average particle size shall be understood herein to mean a size range that applies to at least 90 percent of the particles.

In the scope of the invention, the term "polymers" for filling agent (b2) shall include both homopolymers and copolymers.

The polymer used as filling agent preferably is a polymer having a mean (by weight) molar mass of at least 150,000 g/mol. The polymer can be, for example, a polymer or copolymer of a methacrylic acid ester. According to a particularly preferred embodiment, the at least one polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), and poly(styrene-co-methylmethacrylate). However, the polymer can just as well be selected from the group consisting of polyethylene, polypropylene or polybutadiene. Moreover, the paste can be cross-linked or non-cross-linked.

The inorganic salt that can be used as filling agent (b2) can be a salt that is soluble or insoluble in the polymerizable monomer. Preferably, the inorganic salt is a salt of an element selected from the second main group of the Periodic Table of elements. According to a preferred embodiment, the inorganic salt is a calcium, strontium or barium salt. According to a particularly preferred embodiment, the inorganic salt is calcium sulfate, barium sulfate or calcium carbonate.

The inorganic oxide that can be used as filling agent (b2) can preferably be a metal oxide. According to a preferred embodiment, the inorganic oxide is a transition metal oxide. According to a particularly preferred embodiment, the inorganic oxide is titanium dioxide or zirconium dioxide.

The metal that can be used as filling agent (b2) can, for example, be a transition metal. According to a preferred embodiment, the metal is tantalum or tungsten.

The metal alloy that can be used as filling agent (b2) is an alloy of at least two metals. Preferably, the alloy contains at least one transition metal. According to a particularly preferred embodiment, the alloy comprises at least tantalum or tungsten. The alloy can also be an alloy of tantalum and tungsten.

The filling agent (b2) is insoluble in the polymerizable monomer (b1) having a pH in the range of 5-9. According to the invention, the filling agent (b2) is considered insoluble in the polymerizable monomer (b1) having a pH in the range of 5-9, if the solubility of the filling agent (b2) in the polymerizable monomer (b1) at a temperature of 25° C. is less than 50 g/l, preferably is less than 25 g/l, more preferably is less than 10 g/l, and even more preferably is less than 5 g/l.

The fraction of paste B accounted for by the at least one filling agent (b2) preferably is less than 85% by weight, more preferably is less than 80% by weight, and even more preferably is less than 75% by weight, relative to the total weight of the components contained in paste B. Paste B preferably contains 15-85% by weight, more preferably 15-80% by weight, and even more preferably 20-75% by weight of the at least one filling agent (b2), relative to the total weight of the components contained in paste B.

Moreover, paste B contains at least one peroxide (b3) that is soluble in the polymerizable monomer (b1).

According to the invention, a peroxide (b3) is understood to mean compounds that contain at least one peroxo group (—O—O—). The peroxide (b3) preferably comprises no free acid groups. The peroxide (b3) can be an inorganic peroxide, for example a toxicologically acceptable hydroperoxide, or an organic peroxide.

According to the invention, the peroxide (b3) is considered soluble in the polymerizable monomer (b1) if at least 1 g/l, preferably at least 3 g/l, even more preferably at least 5 g/l, and particularly preferably at least 10 g/l of the peroxide (b3) dissolve(s) in the polymerizable monomer (b1) at a temperature of 25° C.

According to a particularly preferred embodiment, the peroxide (b3) is selected from the group consisting of dibenzoyl peroxide and dilauroyl peroxide.

Paste B preferably contains 0.01-12% by weight, preferably 0.03-10% by weight, more preferably 0.05-8% by weight, and even more preferably 0.1-5% by weight of at least one peroxide (b3), relative to the total weight of the components contained in paste B.

Moreover, paste B comprises at least one heavy metal compound (b4) that is insoluble in (b1) and is selected from the group consisting of heavy metal salts and heavy metal complexes. According to the invention, heavy metal compounds shall be understood to mean metals having a density of at least 3.5, preferably of at least 5, at a temperature of 20° C.

According to a preferred embodiment, the heavy metal compound (b4) that is insoluble in (b1) is a basic heavy metal compound. Basic heavy metal compound shall be understood to mean a heavy metal compound which, when dissolved or suspended in water, has a pH of at least 6.5, preferably at least 7, and even more preferably at least 7.5.

According to a particularly preferred embodiment, the heavy metal compounds are compounds of metals that can change their oxidation state. Copper (II), iron (II), iron (III), manganese (II), manganese (III), cobalt (II), and cobalt (III) compounds are preferred according to the invention.

The heavy metal compounds according to the invention are capable of converting, in the presence of the barbituric acid derivatives (a3), into a form that is soluble in the polymerizable monomer (a1) and/or (a2).

According to the invention, the heavy metal compounds are heavy metal salts or heavy metal complexes. The heavy metal salts preferably are halides, hydroxides, carbonates or carbonic acid salts of heavy metals. Copper (II), iron (II), iron (III), manganese (II), manganese (III), cobalt (II), and cobalt (III) salts are preferred heavy metals salts. According to one embodiment, the heavy metal salt is selected from the group consisting of copper hydroxide, cobalt(II) hydroxide, and basic copper carbonate.

According to a particularly preferred embodiment, the heavy metal compound (b4) that is insoluble in (b1) is a halide salt. According to the embodiment, the need for a halide salt to be present in at least one of the pastes A and B is met by the halide salt that is the insoluble heavy metal compound. Therefore, according to the invention, a halide salt can be both the heavy metal compound that is insoluble in (b1) and the halide salt of paste B that is the halide ion donor. Therefore, the halide salt contained in paste B and the heavy metal compound (b4) that is insoluble in (b1) can be the same compound.

The halide salt can preferably be selected from the group consisting of heavy metal chlorides and bromides. According to a particularly preferred embodiment, the halide salt is a compound selected from the group consisting of copper(II) chloride, manganese(II) chloride, iron(II) chloride, iron(III) chloride, cobalt(II) chloride, and cobalt(III) chloride.

The fraction of paste B accounted for by the heavy metal compound (b4) preferably is in the range from 0.0005-0.5% by weight, more preferably in the range from 0.001-0.05% by weight, and particularly preferably in the range of 0.001-0.01% by weight, relative to the total weight of paste B.

Moreover, at least one halide ion donor is present in either of the pastes A and B.

According to one embodiment, the halide ion donor is a halide salt. The halide salt can be, for example, an inorganic halide salt or an organic halide salt. In these cases, the halide salt preferably is a chlorine or bromine salt.

According to a particularly preferred embodiment, the halide salt is a quaternary ammonium salt of a halide. The quaternary ammonium salt can preferably be a quaternary alkyl, aryl, aryldialkyl, diarylalkyl or cycloalkyl dialkylammonium salt. Trioctylmethylammoniumchloride, for example, is a preferred halide salt.

According to another particularly preferred embodiment, the halide salt can just as well be a hydrohalide, preferably a hydrochloride or hydrobromide. In this context, the halide salt can preferably be a hydrohalide of a tertiary ammonium compound.

According to yet another preferred embodiment, the halide salt can be a halide having a metal cation or a metal oxide cation. Conceivable metal cations are, for example, lithium ($Li^+$) zinc ($Zn^{2+}$), and zirconium ($Zr^{4+}$) cations. Zirconium oxide cation, $ZrO^{2+}$, for example, can be a preferred metal oxide cation. Preferably, the halide salt having a metal cation or metal oxide cation is a halide salt selected from the group consisting of lithium chloride (LiCl), zinc dichloride ($ZnCl_2$), and zirconium oxide dichloride ($ZrOCl_2$).

Moreover, according to another preferred embodiment, the solubility of the halide ion donor in the polymerizable monomer (a1) and/or (b1) that is present in the paste, in which the halide ion donor is present also, is at least 10 g/l, more preferably at least 25 g/l, even more preferably at least 50 g/l, and even more preferably at least 100 g/l.

According to a particularly preferred embodiment, it is feasible that the halide salt is contained in paste B and is identical to the heavy metal compound (b4) that is insoluble in (b1). Therefore, the halide salt contained in paste B and the heavy metal compound (b4) that is insoluble in (b1) can be the same compound. According to the embodiment, it can be preferred that the halide salt is selected from the group consisting of heavy metal chlorides and bromides. According to a particularly preferred embodiment, the halide salt is a compound selected from the group consisting of copper(II) chloride, manganese(II) chloride, iron(II) chloride, iron(III) chloride, cobalt(II) chloride, and cobalt(III) chloride.

The fraction of the respective paste accounted for by the halide ion donor preferably is 0.005-10% by weight, more preferably is 0.001-8% by weight, even more preferably is 0.01-5% by weight, and particularly preferably is 0.3-3% by weight, relative to the total weight of the paste containing the halide ion donor.

If the at least one compound acting as halide ion donor and the at least one heavy metal compound (b4) that is insoluble in (b1) are the same halide salt or the same halide salts, it can be preferred that the fraction of paste B accounted for by the halide salt or halide salts is in the range of 0.005-10% by weight, more preferably in the range of 0.001-8% by weight, even more preferably in the range of 0.01-5% by weight, and particularly preferably in the range of 0.001-0.01% by weight, relative to the weight of paste B.

Moreover, the pastes of the kit according to the invention can comprise additional components.

For example, at least one of the pastes can contain at least one adhesion promoter. The adhesion promoter favors the adhesion of the bone cement to the prosthesis. Methacrylamide, for example, has proven to be a suitable adhesion promoter.

Moreover, at least one of the pastes can comprise at least one cross-linker. The cross-linker preferably is a bifunctional or trifunctional compound. According to the invention, the purpose of the cross-linker is to cross-link the monomer that polymerizes during the curing of the bone cement. According to a preferred embodiment, the cross-linker comprises at least two (meth)acrylate groups. It is particularly preferred for the cross-linker to be selected from the group consisting of ethyleneglycol dimethacrylate, butyleneglycol dimethacrylate (e.g. butane-1,4-diol-dimethacrylate), and hexamethylene dimethacrylate (e.g. hexane-1,6-diol-dimethacrylate).

Moreover, at least one of the pastes can also comprise at least one radiopacifier. The radiopacifier is preferably selected from the group consisting of metal oxides (for example, zirconium oxide), barium sulfate, toxicologically acceptable heavy metal particles (for example tantalum), ferrite, and magnetite (possibly supramagnetic magnetite). The radiopacifiers preferably have a mean particle diameter in the range from 10 nm-500 µm. In addition, it can be expedient to use radiopaque compounds that are soluble in the polymerizable monomer. Examples of such are 3,5-bis(acetamido)-2, 4,6-triiodobenzoic acid esters. It is feasible just as well to integrate gadolinium compounds such as gadolinium chelate with esters of 1,4,7,10-tetraazacyclododecane-1,4,7,10-tetraacetic acid (DOTA), as contrast agent in magnetic resonance imaging in at least one of the pastes.

According to a preferred embodiment, at least one of the pastes, but preferably both pastes, contain(s) at least one polymer that is soluble in the polymerizable monomer contained in the paste(s). According to the invention, the polymer is considered soluble in the polymerizable monomer that is contained in the paste that contains the soluble polymer as well, if at least 10 g/l, preferably at least 25 g/l, more preferably at least 50 g/l, and particularly preferably at least 100 g/l of the polymer dissolve in the polymerizable monomer. The polymer that is soluble in the polymerizable monomer can be a homopolymer or a copolymer. The polymer preferably is a polymer having a mean (by weight) molar mass of at least 150,000 g/mol. The polymer can be, for example, a polymer or copolymer of a methacrylic acid ester. According to a particularly preferred embodiment, the at least one polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), and poly(styrene-co-methylmethacrylate). The fraction of the paste containing the polymer that is accounted for by the polymer that is soluble in the polymerizable monomer preferably is in the range from 5-50% by weight, more preferably in the range from 10-40% by weight, and particularly preferably is in the range from 20-30% by weight.

Moreover, at least one of the pastes can comprise at least one stabilizer. The stabilizer should be suitable to prevent spontaneous polymerization of the monomers contained in the pastes. Moreover, the stabilizer should not undergo interfering interactions with the other components contained in the pastes. Stabilizers of this type are known according to the prior art. According to a preferred embodiment, the stabilizer is 2,6-di-tert-butyl-4-methylphenol and/or 2,6-di-tert-butylphenol.

Moreover, at least one of the pastes can contain at least one pharmaceutical substance. According to a particularly preferred embodiment, paste A contains the pharmaceutical substance. However, the pharmaceutical substance can just as well be contained also or just in paste B, provided it shows sufficient stability with respect to the components contained in paste B. The at least one pharmaceutical substance can be contained in paste A and/or paste B in dissolved or suspended form.

The pharmaceutical substance can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical substance is an antibiotic.

The at least one antibiotic is preferably selected from the groups of aminoglycoside antibiotics, glycopeptide antibiotics, lincosamide antibiotics, gyrase inhibitors, carbapenemes, cyclic lipopeptides, glycylcyclines, oxazolidones, and polypeptide antibiotics.

According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, tinidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

The at least one growth factor is preferably selected from the group consisting of fibroblast growth factor (FGF), transforming growth factor (TGF), platelet-derived growth factor (PDGF), epidermal growth factor (EGF), vascular endothelial growth factor (VEGF), insulin-like growth factors (IGF), hepatocyte growth factor (HGF), bone morphogenetic protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

Moreover, at least one of the pastes can comprise at least one colorant. It is particularly preferred for the colorant to be a food colorant. According to a particularly preferred embodiment, the colorant is selected from the group consisting of E101, E104, E132, E141 (chlorophyllin), E142, riboflavin, and lissamine green. According to the invention, the term, colorants, shall also include color varnishes, such as, for example, color varnish green, the aluminum salt of a mixture of E104 and E132.

According to a particularly preferred embodiment, paste A contains at least 20% by weight polymerizable monomer (a1), at least 20% by weight insoluble filling agent (a2), at least 0.1% by weight barbituric acid derivative (a3), and at least 0.05% by weight halide ion donor, and paste B contains at least 20% by weight polymerizable monomer (b1), at least 20% by weight insoluble filling agent (b2), at least 0.01% by weight soluble peroxide (b3), at least 0.01% by weight heavy metal compound (b4), and at least 0.05% by weight halide ion donor.

According to another particularly preferred embodiment, paste A contains 15-85% by weight polymerizable monomer (a1), 15-85% by weight insoluble filling agent (a2), 0.1-10% by weight barbituric acid derivative (a3), and 0.05-10% by weight halide ion donor, and paste B contains 15-85% by weight polymerizable monomer (b1), 15-85% by weight insoluble filling agent (b2), 0.01-12% by weight soluble peroxide (b3), 0.001-0.05% by weight heavy metal compound (b4), and 0.05-10% by weight halide ion donor.

According to the invention, the purpose of the kit containing at least pastes A and B is the production of bone cement. For this purpose, the at least two pastes A and B are mixed with each other, upon which another paste, paste C, is obtained. The mixing ratio preferably is 0.5-1.5 parts by weight of paste A and 0.5-1.5 parts by weight of paste B. According to a particularly preferred embodiment, the fraction of paste A is 30-70% by weight and the fraction of paste B is 30-70% by weight, relative to the total weight of pastes A and B.

The mixing process can involve common mixing devices, for example a static mixer or a dynamic mixer. The mixing process can proceed in a vacuum. However, the use of the initiator system according to the invention also allows for mixing of pastes A and B in the absence of a vacuum without adverse effect on the properties of the bone cement.

Paste C, which is ultimately obtained after mixing the pastes of the kit, is tack-free according to the ISO 5833 standard and can be processed without delay.

The bone cement generated from paste C by curing attains high strength approximately six to eight minutes after mixing the pastes contained in the kit.

According to a preferred embodiment, the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy.

In this context, the term "spacer" shall be understood to mean implants that can be used temporarily in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that contain bone cement made from the kit according to the invention. Moreover, the carrier materials can also be threaded onto absorbable or non-absorbable suture material in a bead-like manner.

The uses according to the invention of bone cement described above are known from the literature and have been described therein on numerous occasions. According to the invention, the kit is used for the above-described uses in that, preferably, the pastes contained in the kit are mixed with each other to produce a paste that is then used in the above-described uses just like pastes known from the prior art.

The invention shall be illustrated through the examples described in the following, though without limiting the scope of the invention.

EXAMPLES

Various kits for producing bone cement were provided in the examples and used to produce bone cement, and the properties of the bone cements thus obtained were compared.

Example 1 relates to a kit according to an embodiment of the invention containing the two pastes, A and B.

Example 2 relates to a kit according to an embodiment of the invention containing the two pastes, A and B, and, in addition, gentamicin sulfate as an antibiotic.

Reference example 1 relates to a kit that is known from DE 10 2007 050 762 B3 and contains two pastes, A and B.

Reference example 2 relates to a commercially available kit, Palacos® R, containing a liquid component that contains the monomer to be polymerized, and a solid component that contains a polymer as filling agent.

Reference example 3 relates to a commercially available kit, Palacos® R+G, containing a liquid component that contains the monomer to be polymerized, and a solid component that contains a polymer as filling agent. Palacos® R+G differs from Palacos® R in that it contains, in addition, the antibiotic gentamicin sulfate.

a) Providing the Kits:

Of providing the kits of Examples 1 and 2 and Reference example 1, the respective pastes A and B were produced by thorough mixing of the respective components (as specified in Table 1). The kits of Reference examples 2 (Palacos® R; batch 7034) and 3 (Palacos® R+G; batch 7047) were procured from commercial sources.

TABLE 1

Composition of the pastes contained in the kits of Examples 1 and 2 and Reference example 1.

| Component | Example 1 Paste A | Example 1 Paste B | Example 2 Paste A | Example 2 Paste B | Reference example 1 Paste A | Reference example 1 Paste B |
|---|---|---|---|---|---|---|
| Methylmethacrylate | 16.2 g | 16.2 g | 16.2 g | 16.2 g | 16.2 g | 16.2 g |
| Methacrylamide | 0.4 g | 0.4 g | 0.4 g | 0.4 g | 0.4 g | 0.4 g |
| Ethyleneglycol dimethacrylate | 0.6 g | 0.6 g | 0.6 g | 0.6 g | — | — |
| Zirconium dioxide | 2.4 g | 2.4 g | 2.4 g | 2.4 g | 2.8 g | 4.0 g |
| Soluble poly(methylmethacrylate-co-methylacrylate) | 10.0 g | 10.0 g | 10.0 g | 10.0 g | 10.6 g | 10.8 g |
| Insoluble polymethylmethacrylate | 9.0 g | 9.0 g | 8.0 g | 9.0 g | 8.4 g | 8.6 g |
| 2,6-Di-t-butyl-4-methyl-phenol | 20 mg | — | 20 mg | — | 20 mg | 20 mg |
| Aliquat 336 (trioctylmethyl ammoniumchloride) | 250 mg | 250 mg | 250 mg | 250 mg | — | — |
| 1-Cyclohexyl-5-ethyl-barbiturate | 1.5 g | — | 1.5 g | — | 1.6 g | — |
| Copper(II) hydroxide | — | 1.0 mg | — | 1.0 mg | — | — |
| Copper(II)-2-ethylhexanoate | — | — | — | — | — | 1 mg |
| Dibenzoylperoxide | — | 0.5 g | — | 0.5 g | — | — |
| Gentamicin sulfate | — | — | 1.0 g | — | — | — |
| Total heavy metal content | <10 ppm | | <10 ppm | | not determined | | b) Production of Bone Cement Using the Kits

In Examples 1 and 2 and Reference example 1, pastes A and B of the respective kit were mixed with each other thoroughly at a mixing ratio of 1:1. The mixtures thus obtained were then introduced into rectangular molds with a height of 3.3 mm and left therein until curing was complete.

The solid components and liquid components of the respective kits in Reference examples 2 and 3 were mixed vigorously using a vacuum mixing device. The mixtures thus obtained were then introduced into rectangular molds with a height of 3.3 mm and left therein until curing was complete.

c) Properties of the Bone Cement Thus Obtained

For the 4-point flexural strength test and flexural modulus test, strips with a length of 75 mm and a width of 10 mm were sawed from the cement plates obtained after curing was completed. The 4-point flexural strength test and flexural modulus test were carried out using a Zwick Universal testing apparatus after storing the test bodies exposed to air for 24 hours at 23° C.

Cylindrical test bodies with a height of 12 mm and a diameter of 6 mm were produced for the test of compressive strength. This measurement also was carried out using a Zwick Universal testing apparatus after storing the test bodies for 24 hours at 23° C.

The results of these tests are shown in Table 2.

TABLE 2

Results of the 4-point flexural strength and flexural modulus tests on the bone cements after 24 hr of storage exposed to air.

| Cement | 4-point flexural strength | Flexural modulus [MPa] |
|---|---|---|
| Example 1 | 70.5 ± 1.7 | 2730 ± 17 |
| Example 2 | 57.5 ± 2.8 | 2350 ± 66 |
| Reference example 1 | 47.0 ± 1.5 | 1809 ± 81 |
| Reference example 2 | 68.6 ± 0.7 | 2925 ± 50 |
| Reference example 3 | 69.0 ± 1.3 | 2945 ± 52 |

In addition, some test bodies were stored in water at 37° C. for 48 hours right after their production. Subsequently, the 4-point flexural strength and the flexural modulus were determined as described above. The results of these tests are shown in Table 3.

TABLE 3

Results of the 4-point flexural strength and flexural modulus tests on the bone cements after 48 hr of storage in water.

| Cement | 4-point flexural strength | Flexural modulus [MPa] |
|---|---|---|
| Example 1 | 79.6 ± 5.2 | 3035 ± 74 |
| Example 2 | 69.4 ± 3.4 | 2726 ± 58 |
| Reference example 1 | 68.6 ± 1.8 | 2577 ± 94 |
| Reference example 2 | 74.0 ± 1.3 | 2882 ± 46 |
| Reference example 3 | 66.5 ± 1.4 | 2774 ± 39 |

As is evident from Table 2, the bone cements of Examples 1 and 2, which were produced using the kit according to embodiments of the invention, show clearly higher 4-point flexural strength and a clearly higher flexural modulus after 24 hr of storage, as compared to the bone cement that is known according to the prior art and is also based on the use of two pastes (Reference example 1). This demonstrates the much increased initial stability of the paste system according to the invention. In particular, the bone cements of Examples 1 and 2, which were produced using the kit according to the invention, show 4-point flexural strength and flexural modulus values after 24 hr of storage comparable to those of conventional kits comprising a solid component and a liquid component, but without the prevailing disadvantages that are associated with the latter systems (e.g. expensive vacuum mixing systems, poisonous monomer vapors).

Table 3 shows that the stability of the bone cement obtained decreases dramatically in disadvantageous fashion during storage in water, which ultimately is to simulate the transplantation environment, in the systems known according to the prior art according to Reference example 1, unlike with the systems according to the invention and the known systems comprising a solid component and a liquid component.

Table 4 shows the relationship of the 4-point flexural strength and flexural modulus values after 24 hr of storage exposed to air and the 4-point flexural strength and flexural modulus values after 48 hr of storage in water (initial 4-point flexural strength and initial flexural modulus).

TABLE 4

Initial 4-point flexural strength and initial flexural modulus of the bone cements obtained in Examples 1 and 2 and Reference example 1.

| Cement | Initial 4-point flexural strength [MPa] | Initial flexural modulus [MPa] |
|---|---|---|
| Example 1 | 88.6% | 90.0% |
| Example 2 | 82.9% | 86.2% |
| Reference example 1 | 68.5% | 66.4% |

Table 4 shows for the bone cement produced with the kit according to embodiments of the invention that the 4-point flexural strength and the flexural modulus are established significantly earlier, in advantageous fashion, than in the bone cement known according to the prior art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A kit comprising a paste A and a paste B, wherein:
 (a) paste A contains:
  (a1) a polymerizable monomer having a pH in water in a range of 5-9;
  (a2) a filling agent insoluble in (a1); and
  (a3) a barbituric acid derivative selected from the group consisting of 1,5-disubstituted barbiturates, 1,3,5-trisubstituted barbiturates, and 1,3,5-tetrasubstituted barbiturates; and
 (b) paste B contains:
  (b1) a polymerizable monomer having a pH in water in a range of 5-9;
  (b2) a filling agent insoluble in (b1);
  (b3) a peroxide soluble in (b1);
  (b4) a heavy metal compound insoluble in (b1) and selected from the group consisting of heavy metal salts and heavy metal complexes; and
 wherein at least one of the pastes A and B contains a halide salt.

2. The kit according to claim 1, wherein the polymerizable monomer in paste A comprises a methacrylate monomer.

3. The kit according to claim 1, wherein paste A further contains a polymer soluble in (a1).

4. The kit according to claim 1, wherein the insoluble filling agent (a2) comprises a particulate polymer.

5. The kit according to claim 1, wherein the polymerizable monomer in paste B comprises a methacrylate monomer.

6. The kit according to claim 1, wherein paste B further contains a polymer soluble in (b1).

7. The kit according to claim 1, wherein the insoluble filling agent (b2) comprises a particulate polymer.

8. The kit according to claim 1, wherein the heavy metal compound (b4) insoluble in (b1) comprises a basic heavy metal compound.

9. The kit according to claim 1, wherein the halide salt is contained in paste B and is the same as the heavy metal compound (b4) insoluble in (b1).

10. A method comprising providing a kit according to claim 1, and applying a mixture of paste A and paste B to a bone substrate.

11. The method of claim 10, wherein the bones substrate has at least one cavity.

12. The method of claim 10, wherein the bone substrate comprises a femur.

13. The method of claim 10, wherein the bones substrate comprises a vertebrae.

14. A method comprising providing a kit according to claim 1, and applying a mixture of paste A and paste B to a prosthetic substrate.

* * * * *